United States Patent [19]
Rizvi

[11] Patent Number: 5,818,046
[45] Date of Patent: Oct. 6, 1998

[54] MID-INFRARED ANALYSIS SYSTEM

[76] Inventor: Syed A. Rizvi, 3850 Downers Dr., Downers Grove, Ill. 60515

[21] Appl. No.: 708,078

[22] Filed: Aug. 30, 1996

[51] Int. Cl.$^6$ .................................................. G01N 21/35
[52] U.S. Cl. ................................ 250/339.12; 250/339.11; 250/341.8
[58] Field of Search ......................... 250/339.11, 339.12, 250/341.8

[56] References Cited

U.S. PATENT DOCUMENTS

| | | |
|---|---|---|
| 3,415,602 | 12/1968 | Harrick . |
| 3,420,138 | 1/1969 | Hansen . |
| 3,460,893 | 8/1969 | Wilks, Jr. . |
| 4,456,374 | 6/1984 | Langberg . |
| 4,490,618 | 12/1984 | Cielo . |
| 4,668,300 | 5/1987 | Miller . |
| 4,732,475 | 3/1988 | Harrick . |
| 4,815,844 | 3/1989 | Schmalfuss et al. . |
| 5,015,092 | 5/1991 | Sting . |
| 5,093,580 | 3/1992 | Sting . |
| 5,185,640 | 2/1993 | Wilks, Jr. et al. . |
| 5,196,901 | 3/1993 | Champetier . |
| 5,216,244 | 6/1993 | Esaki et al. . |
| 5,278,413 | 1/1994 | Yamaguchi et al. . |
| 5,338,935 | 8/1994 | Truett et al. ........................ 250/339.06 |
| 5,506,416 | 4/1996 | Rizvi . |
| 5,569,921 | 10/1996 | Sato et al. .......................... 250/339.01 |

FOREIGN PATENT DOCUMENTS 55-101848A  8/1980  Japan .

*Primary Examiner*—Constantine Hannaher
*Attorney, Agent, or Firm*—Welsh & Katz, Ltd.

[57] ABSTRACT

A set of mid-infrared transparent elements with new element geometry, design of the optics and radiation path configuration is described. Radiation from the IR microscope objective, after being internally reflected at the element/sample interface is either returned to the objective or is directed through the microscope condenser optics with sample information to the detector system for spectral analysis. Alternatively, the beam may bounce off the element/sample interface either once, twice or multiple times at the same angle of incidence, to allow examination of the micro surface of the sample by internal reflectance as well as transmission of the beam through the same sample area. Further, a method to perform external reflectance measurements at different angles of incidence using the described apparatus is discribed.

17 Claims, 7 Drawing Sheets

AT 45°

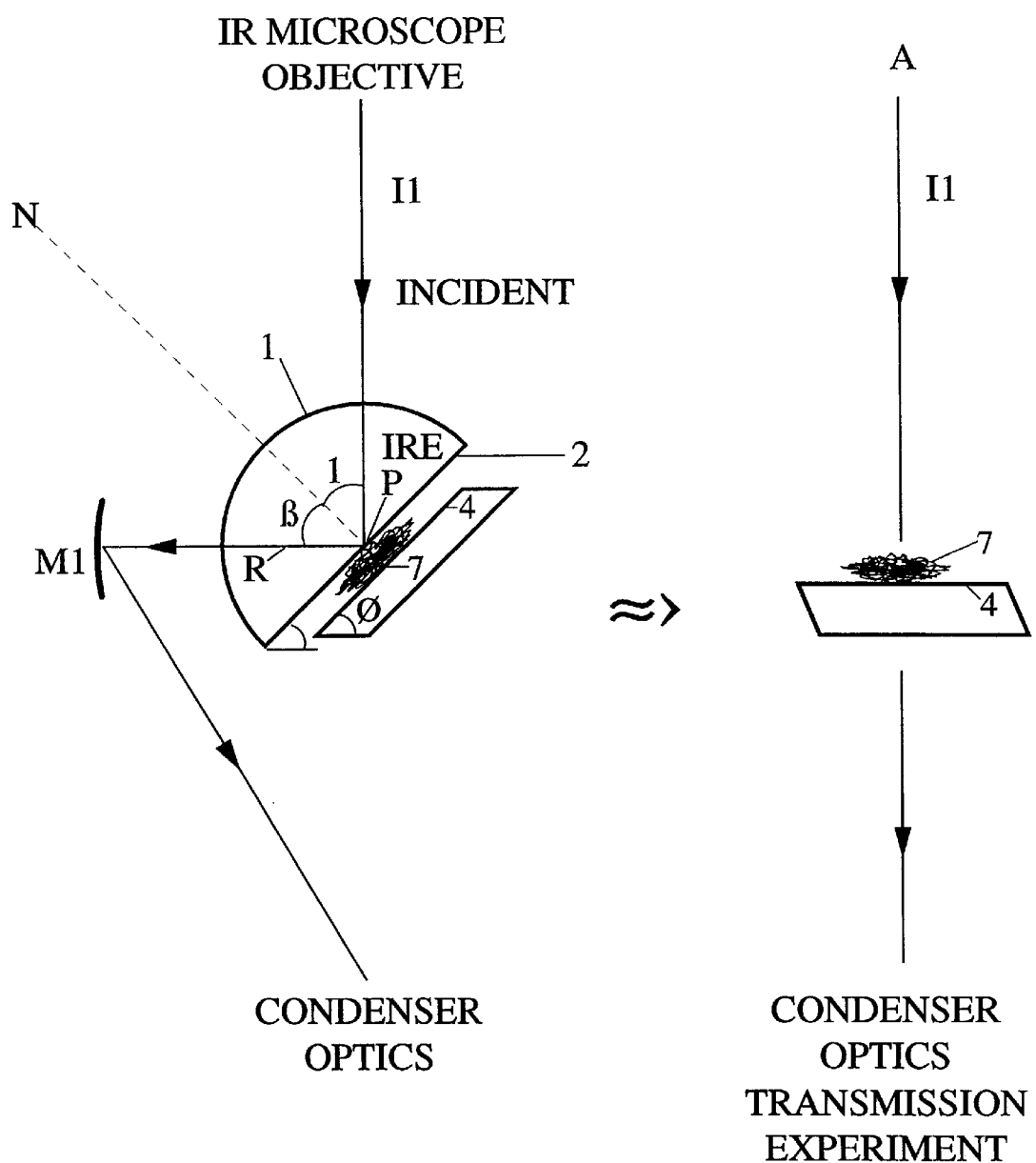

MID-INFRARED ANALYSIS SYSTEM

BACKGROUND OF THE INVENTION

This application relates to an apparatus and method for using attenuated total reflectance spectroscopy to analyze the surface defects of polymer surfaces.

Elements with different geometry and radiation path configurations are developed to allow examination of micro surface areas at different depths of penetration. The infrared (IR) beam enters and leaves the device in such a way that the radiation losses are minimized.

The beam, after entering the element, interacts with the sample in contact with the element at an angle above the critical angle to enable examination of the sample surface at a certain depth controlled by the angle of incidence of the IR beam and the refractive index of the Internal Reflectance Element (IRE). The beam then leaves the element and is forwarded to a detection system for analysis.

SUMMARY OF THE INVENTION

In the subject invention, significant change in the optical design of the light path has been made to enable internal reflectance analysis of a trace amount of the surface of a sample of interest. The sample is examined both optically and spectroscopically. The radiation from the spectrometer source entering the IR microscope tandem to the spectrometer reaches the internal reflectance element unobstructed, interacts with the sample surface once, twice or more times and is directed through the beam condenser optics of a microscope or by suitable means to the detector. Beam condenser optics focus the radiation to a tight beam for maximum light and analysis. The design further allows a) external reflectance measurements at selected angles of incidence including grazing angles and b) transmission analysis of the same trace sample area. In one embodiment where the microscope is operational in the reflectance mode, the partially blocked beam emerging from the microscope launching optics is directed to enter the element at an angle above the critical angle, is internally reflected at the element/sample interface and is configured to return to the objective whereby the beam follows a different path to reach the detector. The critical angle may be defined as that angle above which total internal reflectance occurs.

In one embodiment of the subject invention, the internally reflected beam emerging from the element/sample interface is deflected by a mirror or a set of mirrors towards the microscope condenser optics to reach the detector similar to when the microscope is set up for analysis in the transmission mode. In a second embodiment, where a special optical design is formulated, the incident beam, after internally interacting with the sample surface at a certain angle of incidence, leaves the element and is directed by the first mirror placed outside of the element to a second mirror which is positioned to return the beam into the element to strike the element/sample interface at the initial point of interaction at the initial angle of incidence. This beam which is then internally reflected for the second time at the element/sample interface, emerges out of the IRE, is directed by a third mirror or a set of mirrors placed outside the IRE and is guided through a condenser to a detector. The path of the beam from the condenser assembly is the same as that when the IR microscope is set up for transmission analysis. The process for the second reflection bounce can be repeated to achieve multiple bounces at the same sample interface. Alternatively, the internally reflected beam from the element/sample beveled interface is directed to built in surfaces of the IRE to guide the beam within the IRE to allow a second bounce at the element/sample interface. In the third case, the radiation from the IR objective after interaction with the sample is returned to the detector through the IR objective in the same way when the microscope is set up for analysis in the reflectance mode.

These methods enable examination of a trace surface at different angles of incidence by using either a single, double or multiple bounce technique to enhance the signal quality. Element configurations and related optical designs in these inventions provide unique opportunities to examine a trace surface of the sample. These techniques not only allow trace surface analysis but also provide capability to acquire trace sample transmission spectra of the same area examined by internal reflectance.

In a fourth embodiment, micro external reflectance measurements are made by simply moving out (displacing) the IRE from the radiation path of the original micro ATR (attenuated total reflectance) set up as shown in FIG. 1 to allow the beam to directly impinge the sample/reflecting metal surface at a selected angle (FIG. 4). The polished metal surface of the sample holder serves as the substrate for reflecting the impinging radiation. The beam from the IR microscope objective after interaction with the sample is reflected by the metal substrate to a mirror assembly positioned to direct the beam with sample information by appropriate transfer optics (condenser optics) to the detector. In this configuration the angle of incidence can be changed from lower angles all the way to the grazing incidence. Energy losses are minimized in these procedures.

Significant improvement in signal to noise is gained by these methods when performing ATR or external reflectance analysis by directing the emerging beam from the sample through the condenser optics or by appropriate transfer mechanism to the detector rather than using the reflectance set-up where a significant portion of the beam is blocked to accomplish angular bounce at the element/sample interface. In the present method the entire beam entering the microscope is utilized resulting in minimum radiation losses during the measurement process.

These techniques provide the capability to examine trace surface defects normally observed in polymer materials such as bloomed components from polymer sample matrix, gel particles, smudges and domains. Opaque samples, tissue samples, single fibers, biological samples and forensic samples can be easily characterized by any of these techniques available. These methods are suitable for analysis with minimum sample preparation and can be suited to fit any IR microscope with only minor modifications.

Therefore, an object of the subject invention is the focal analysis of the surface of transparent films and opaque particles.

A further object of the invention is spectral analysis of transparent or opaque surfaces by depth profiling.

There are other objects of the subject application attained by an apparatus and method which uses parts of the invention to perform external reflectance measurements at different angles of incidence and transmission spectroscopy of the same sample area.

Thallium bromoiodide (KRS-5), zinc selenide, germanium or other transparent materials in the spectral region of interest can be used for internal reflectance measurements.

Metal substrates with high reflectivity are generally used for external reflectance measurements. Polymer substrates may also be suitable for thin film analysis.

The IRE is mounted on a travel guide to facilitate movement in the x-y-z directions; similarly the position of the sample holder can be moved in the x, y and z directions for optical examination. All the mirrors used have the capability of movement in x, y and z planes to aim the beam to strike the sample mirrors and go through the condenser optics or other beam guiding means for guiding the beam to the detection apparatus. Once the sample area for the analysis is selected, then the position of the sample holder remains fixed for data acquisition.

BRIEF DESCRIPTION OF THE DRAWINGS

Several forms of the novel apparatus of the subject invention will now be described in greater detail with reference to the annexed drawings in which:

FIG. 7 is a schematic of a sample holder made from an IR transparent material for transmission analysis.

FIG. 8 is a schematic of an IRE of the prior art.

DETAILED DESCRIPTION OF THE DRAWINGS

The principle of internal reflectance is utilized in acquiring information on a surface of a very small size.

As stated, the subject invention can include an internal reflectance element which allows the examination of trace amount of sample surface spectroscopically at selected angles of incidence at the IRE/sample interface. These elements can be fabricated from any of the available transparent materials having different indices of refraction in the spectral region of interest. This added flexibility in the choice of IRE materials combined with the ability to change the angle of incidence gives control over the depth of penetration of the radiation into the trace sample surface.

The size of the IRE is not critical. An element which can be placed on the microscope stage and examined through the microscope is required. Thus, the sample can be optically as well as spectroscopically examined not only in the IR but also in other spectral regions.

Figure 1:
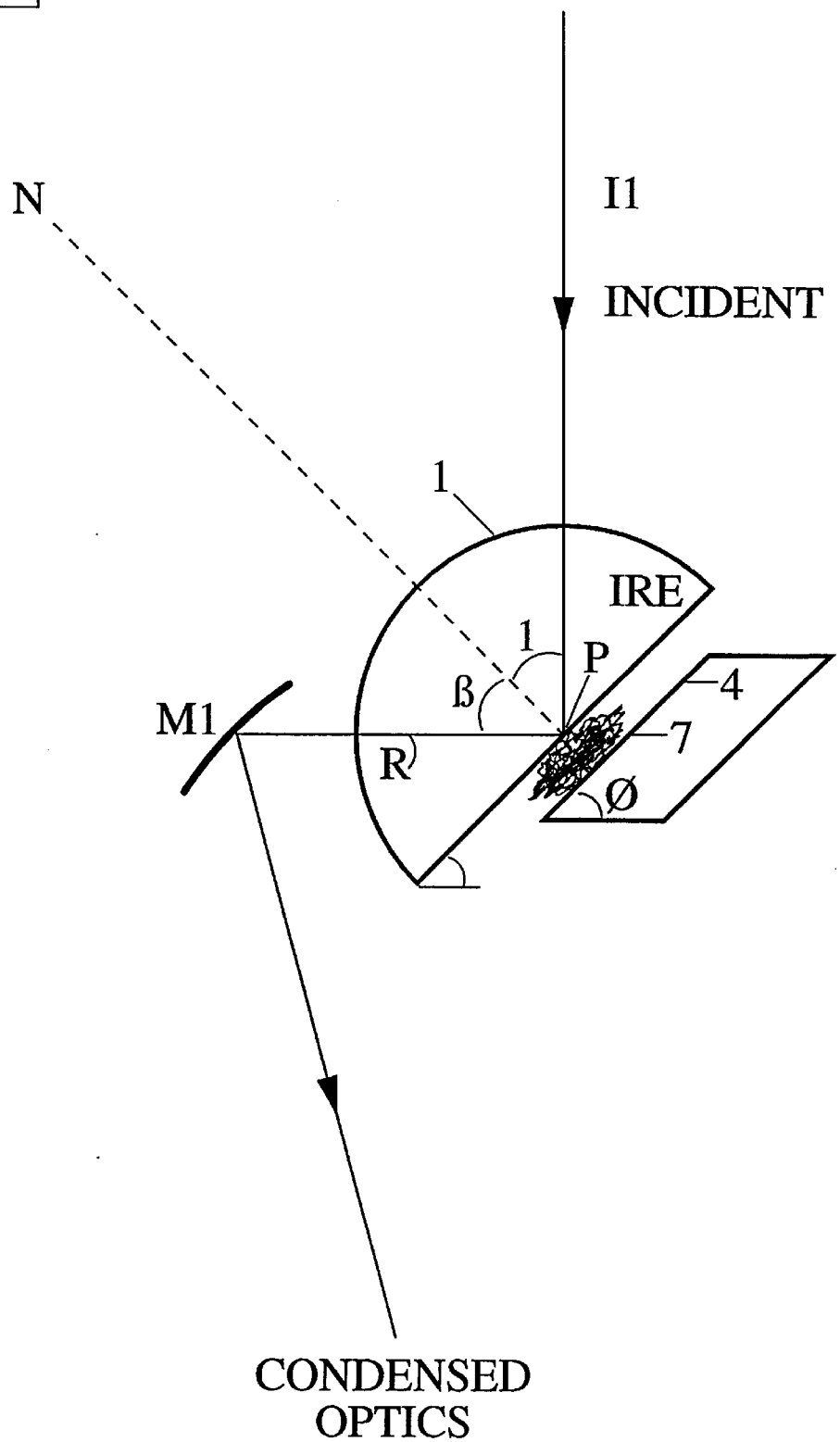
FIG. 1 is a schematic of a hemispherical IRE with sample holder and mirror used with the subject invention.

The subject invention is a hemispherical IRE as shown in FIG. 1 with a circular outer surface 1 having the center of curvature at a point P along the side 2. Further, the IRE may have flattened sides (not shown). FIG. 1 is a modified version of IRE assembly described in the prior art embodiment of FIG. 8.

The incident beam I1 of the IRE of FIG. 1 enters the IRE and impinges the surface 2 at an angle $\alpha$, above the critical angle, to the normal N at some point P. N is the line perpendicular to the surface 2 at P. This beam is then internally reflected at a given angle and travels along path R, strikes the mirror M1 and is reflected through the condenser optics or by other suitable beam guiding means to the detector. It is not always necessary to have condenser optics. Other beam guiding mechanisms may be substituted.

A metal sample holder with polished surface 4 allows optical and spectroscopic examination of sample 7. Angle $\alpha$, $\beta$ and $\tau$ are identical. The sample holder surface 4 is inclined at an angle $\phi$ and is positioned as shown in FIG. 1 to make a continuous contact along surface 2 of the IRE. Angle $\phi$ of the sample holder and angle $\tau$ of the IRE are identical.

The sample holder and the IRE are mounted on rails (not shown) as known in the art. The sample holder maintains a fixed position during the data acquisition mode but the IRE can be moved forward and backwards in the x direction by an appropriate mechanism, as known in the art. The IRE is moved in the forward direction to come in contact with the sample as shown in FIG. 1.

In this particular case for demonstration purpose a 45 degree angle is selected. The IR beam is allowed to strike the IRE/sample interface at 45 degrees. Angle $\alpha$, $\beta$ and $\tau$ are 45 degrees.

Figure 2:
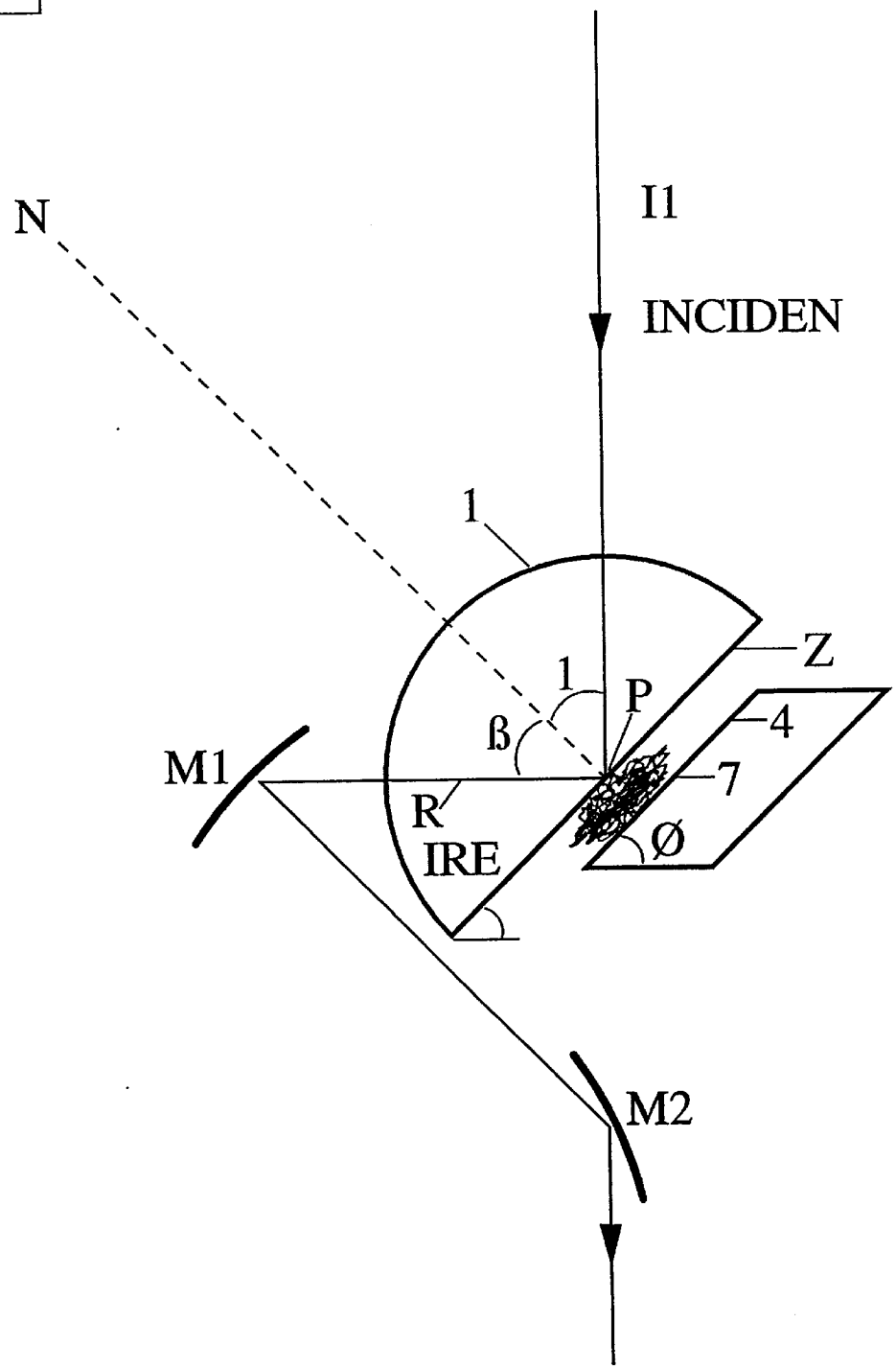
FIG. 2 is a schematic of a hemispherical IRE similar to that in FIG. 1 with sample holder and two mirrors with the subject invention.

FIG. 2 is similar to FIG. 1 except that mirror M21 directs the incident beam I2 to mirror M22 which in turn aims the beam to the condenser optics and then to the detector.

Figure 3:
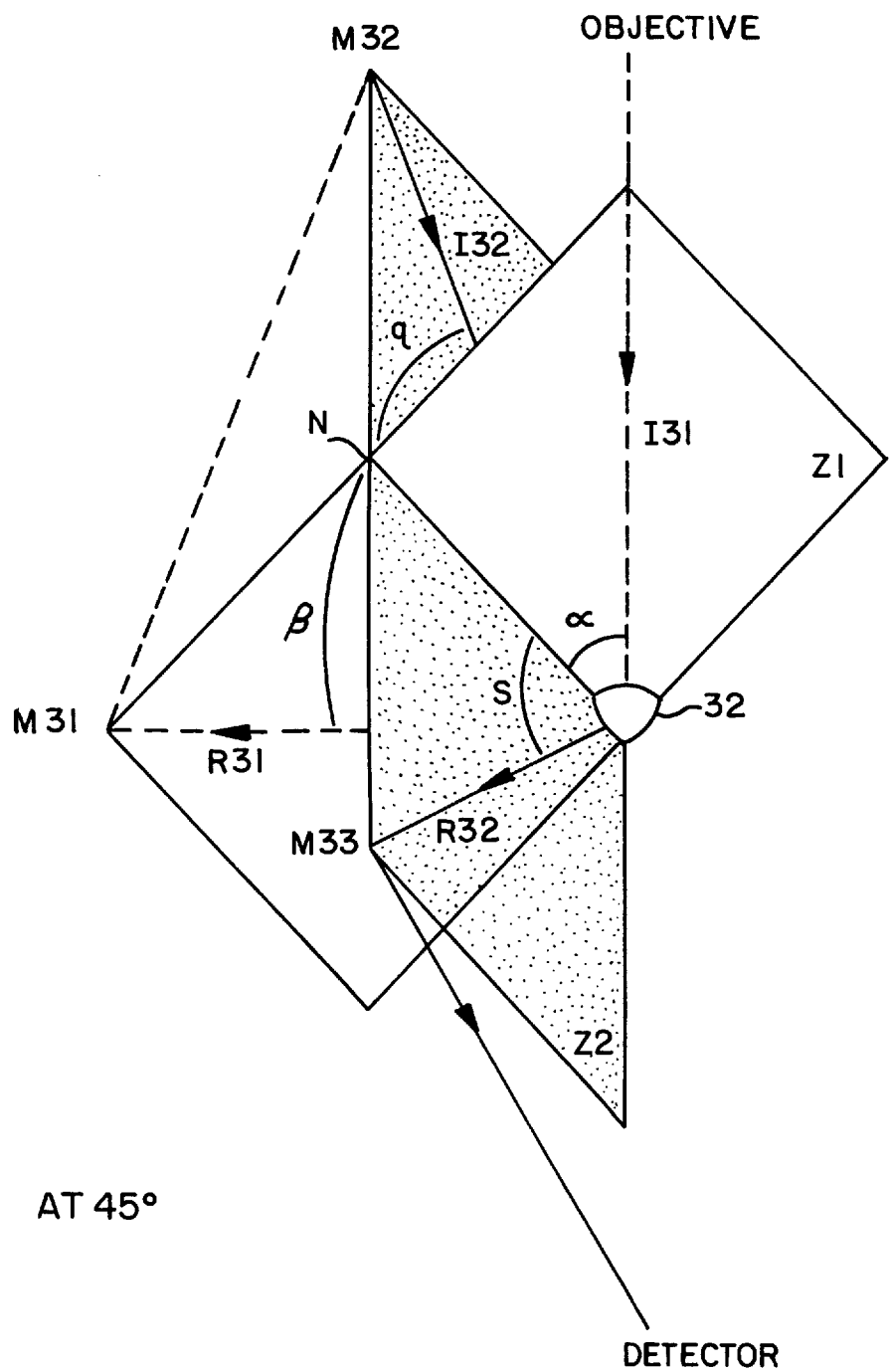
FIG. 3 is a schematic of a hemispherical IRE similar to that in FIG. 1 with sample holder and a set of reflecting surfaces in a specific configuration. A radiation path of two geometrically different planes is presented.

FIG. 3 represents a radiation path which allows interaction of the beam at the IRE/sample interface twice, i.e., a double bounce operation. The incident beam I31 from the IR objective mirror assembly enters the hemispherical IRE as shown in FIG. 3. I31 impinges at a point P on surface 32 at an angle $\alpha$, above the critical angle, and is internally reflected to follow the path R31. The normal at point P is N. The path of the beam I31-P-R31-M31 is contained by plane Z1 as shown in the figure. Angles $\alpha$, $\beta$ and $\tau$ are identical. This beam emerges out of the IRE, strikes the mirror M31 which is positioned to deflect the beam to a second external mirror M32 which is oriented to redirect the beam I32 to reenter the IRE to impinge at point P at the IRE/sample interface. The incident beam I32 is adjusted to make an angle of incidence q at point P such that angles q, s, $\alpha$, $\beta$, $\tau$ and $\phi$ are identical as defined in FIG. 1. The internally reflected beam then follows the path R32. The reflected beam from M32 represented by M32-I32-R32-M33 is contained by a second plane Z2. Hence, the beam entering and leaving the IRE for the second bounce is contained by a different plane as shown in FIG. 3. The normal N and point P is common to and is contained by both planes. The beam under these conditions strikes the sample surface twice at the same angle of incidence. After the second bounce the emerging beam R32 is guided towards the condenser assembly either directly from mirror M33 or via another mirror through the condenser or by other means to the detector. The second bounce process can be repeated to accomplish multiple bounces at the same position on the sample surface at the same angle of incidence.

Sampling is accomplished by moving the IRE forward to come in contact with the sample placed on the sample holder in the same way as shown in FIG. 1. Alternatively, second and third built in surfaces of the IRE (not shown) can be utilized to guide the beam within the IRE to accomplish the second bounce at the element/sample interface. The beam after the second interaction with the sample is directed out of the IRE towards the detector.

Figure 4:
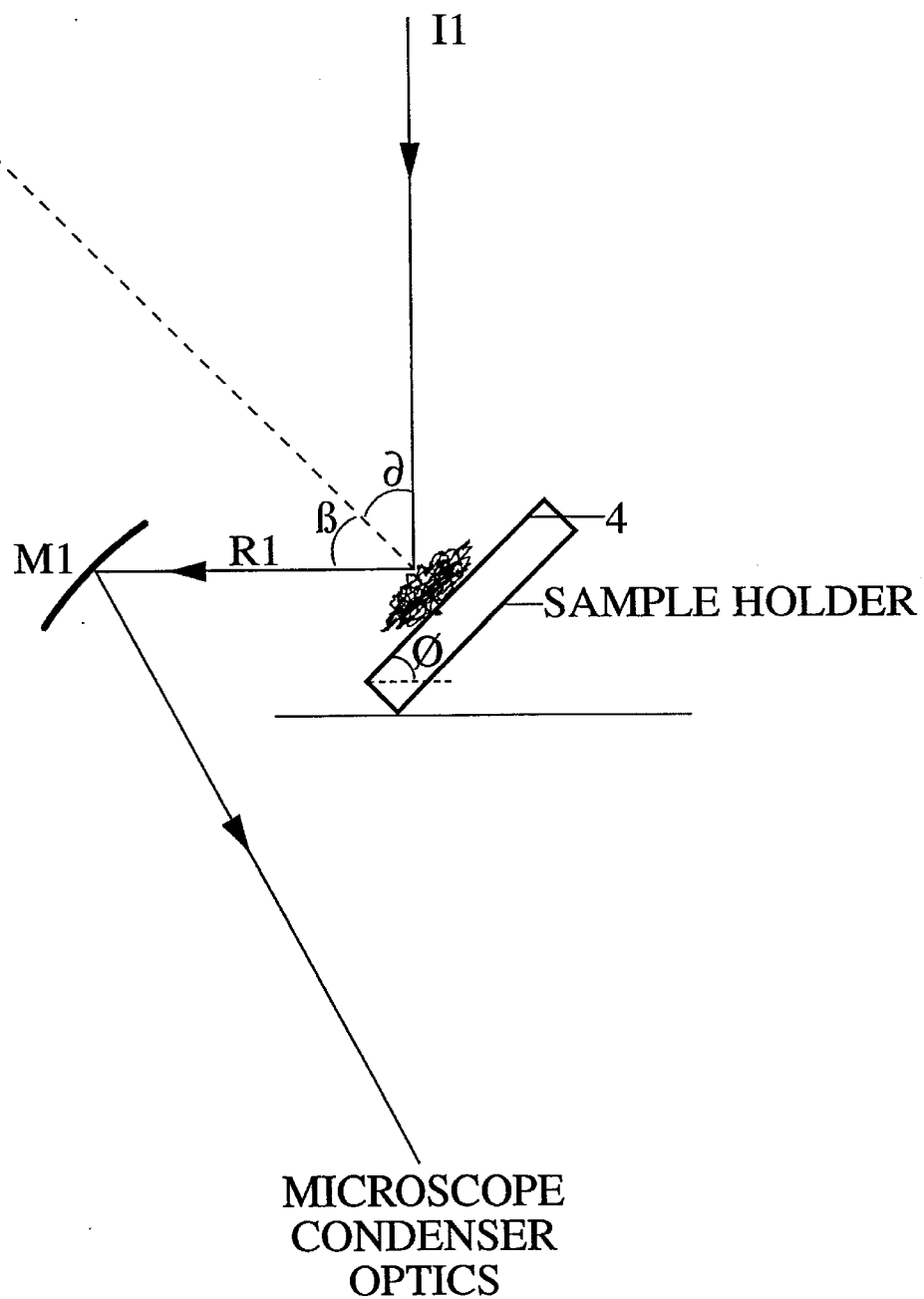
FIG. 4 is a schematic of the apparatus for external reflectance measurements.

FIG. 4 shows an apparatus for analysis by external reflectance. This apparatus is generally the same as that described in FIGS. 1 and 2, without the IRE. A sample can be optically and spectroscopically analyzed using this device. The beam I4 from the microscope objective impinges directly on the sample placed on the polished surface of the sample holder. The reflected beam R10 is directed to a mirror M41 where it is deflected directly or through a second mirror M42 to the condenser optics and on to the detector. The polished sample holder is pivotable, thereby allowing the beam to impinge the sample surface at any selected angle φ. With this arrangement, measurements at grazing angles can be made. The sample holder plate is kept horizontal during optical examination. After optical examination the plate can be rotated about the sample axis for data acquisition at selected angles.

Figure 5:
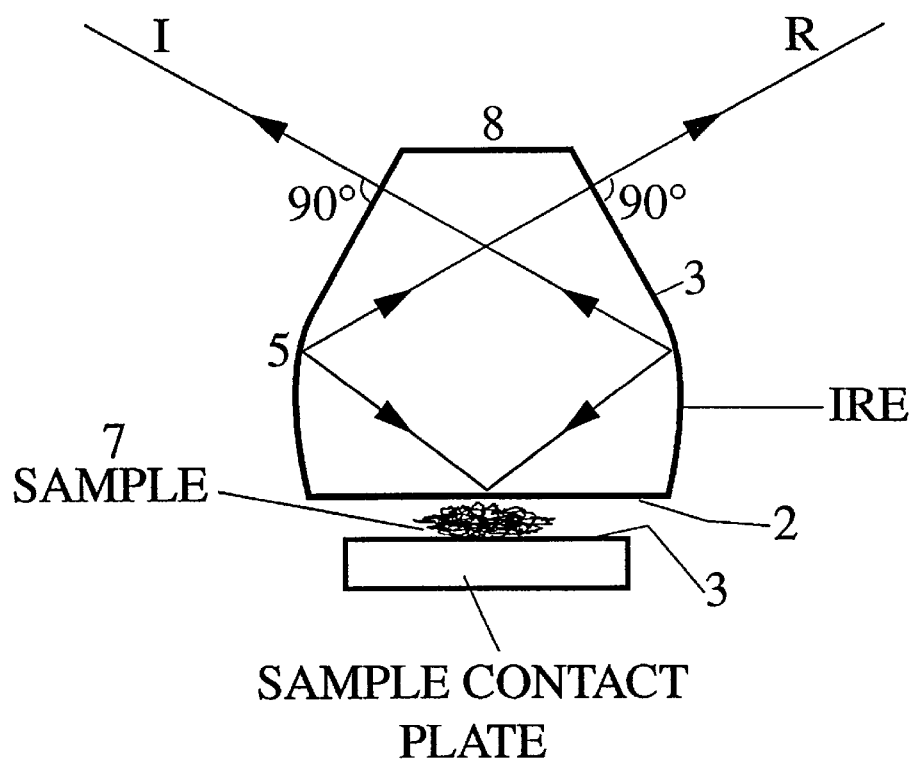
FIG. 5 is schematic of a different design of IRE.
Figure 6:
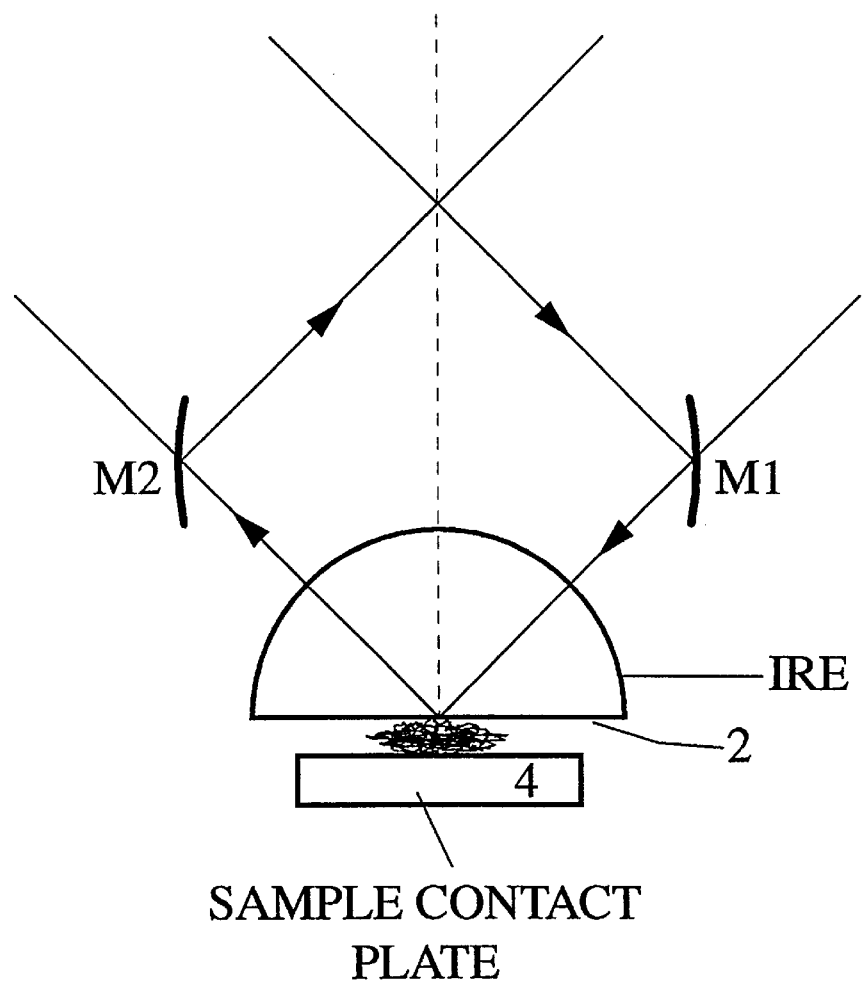
FIG. 6 is the schematic of another design of a IRE with a set of mirrors.

FIG. 5 depicts a further embodiment of an IRE pursuant to the subject invention. The incident beam I5 from the IR microscope objective enters the IRE at surface 51 at ninety degrees, strikes the curved surface 53 such that it is internally reflected and directed to the IRE/sample interface at an angle above the critical angle a at point PS where it is internally reflected to strike the curved surface 55 and is again internally reflected to emerge at flat surface 56 at right angle and is routed to the IR microscope objective to reach the detector. Sample contact plate K with the sample on surface 54 can be lowered or raised. The adjustable mechanism of the sample contact plate is utilized to press the sample against the IRE surface 52 for spectral examination FIG. 6 is an alternative embodiment where the incident beam I-6 from the IR microscope objective strikes mirror M61 which directs the beam to enter the IRE and impinge the IRE/sample interface at point P-6 above the critical angle α. The internally reflected beam R-6 then emerges out of the IRE to reach mirror M62 which aims the beam through the microscope objective towards the detector. Sample contact plate K-6 with the sample on surface 64 can be lowered or raised. The adjustable mechanism of the sample contact plate is utilized to press the sample against the IRE surface 62 for spectral examination.

FIG. 7 is similar to that shown in FIG. 1. The sample holder is of an IR transparent material. The IRE is moved out of the incident beam path and the sample holder is rotated clockwise to acquire a horizontal position to allow the incident IR beam I7 to strike the sample at a right angle and is transmitted through the sample holder 74 (IR window) to acquire the transmission spectrum of the sample.

While the invention has been described with reference to a preferred embodiment, it will be understood by those skilled in the art that various changes may be made and equivalence may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalence falling within the scope of the appended claims.

Various features of the invention are set forth in the following claims.

What is claimed:

1. A method of spectroscopically analyzing a sample surface comprising the steps of: directing a source of infrared light at a certain angle of incidence above the critical angle to a point on an interface between a hemispherical internally reflective element and a sample so that a light beam is internally reflected from said point to a mirrored surface or surfaces external or internal to said reflective element along a light path, positioning said mirrored surface and said internally reflective element and sample interface relative to each other, and adjusting the position of said hemispherical internal reflectance element to cause said internally reflected light beam to go to a detection system.

2. The method of claim 1 further including the step of adjusting the position of said internal reflectance element and sample interface.

3. An Internal Reflectance Element for use in internal reflectance spectroscopy, comprising:

a transparent element;

a sample holder;

said transparent element having a spherical exterior surface and beveled internal reflectance surface at a first angle with respect to the x-y plane, said sample holder forming a second angle equal to said first angle, said element being pivotable to change said first angle to a desired angle;

said sample holder maintaining a sample in a position for optical and spectroscopic analysis on a beveled internal reflectance element sample interface, said beveled internal reflectance element/sample interface being at an angle equivalent to said second angle;

an external mirrored surface spaced from said beveled internally reflectance element/sample interface and positioned at a third angle relative to said beveled internal reflectance element/sample interface, so that a full and direct IR beam enters said internal reflectance element along a path, and strikes at a point creating fourth and fifth angles to be directed to strike said external mirrored surface and be reflected to a detection system for analysis.

4. The Internal Reflectance Element of claim 3 wherein said external mirrored surface reflects the IR beam to a second mirrored surface which directs the beam to a detection device.

5. The Internal Reflectance Element of claim 3 having an internal reflectance surface to guide the beam out of the IRE to a detection device.

6. The Internal Reflectance Element of claim 3, wherein said mirrored surface is movable in the x, y and z planes to compensate for the path of said incident light beam.

7. The Internal Reflectance Element of claim 3 wherein said transparent optical element and said sample holder are movable in x, y and z planes.

8. An Internal Reflectance apparatus for use in internal reflectance spectroscopy, comprising:

a transparent element;

a sample holder;

said transparent element having a spherical exterior surface and a beveled internal reflectance surface at a first angle with respect to the x-y plane, said sample holder forming a second angle equal to the first, said element being pivotable to change said first angle to another angle;

said sample holder maintaining a sample in position for optical analysis by an IR beam on a beveled internal reflectance element/sample interface, said beveled internal reflectance element/sample interface being at an angle equivalent to said second angle;

said spherical element having an internally reflecting surface;

said spherical element having first, second and third external mirrored surfaces positioned to direct the IR beam in and out of the internal reflectance element, so that an IR beam can enter said transparent element at an entry point and travel along a path, strike said internal reflectance surface above the critical angle, to interact with the sample at a point, be directed to strike said first external mirrored surface, be reflected to strike said second external mirrored surface, be reflected to reenter the internal reflectance element at a second entry point and travel along a path, strike said element at said point, be reflected to said third external mirrored surface for reflection to a detector means for analysis.

9. The Internal Reflectance Element of claim 8 wherein additional external mirrors reflect the IR beam for additional strikes of said point for multisampling of the IRE sample interface.

10. The Internal Reflectance Element of claim 8 wherein a line drawn perpendicular to said surface at said point creates fourth and fifth angles with said incident IR beam and said reflected beam at the normal at the said point for the first strike and sixth and seventh angles with said reentering IR beam into said Internal Reflectance Element, wherein said second, fourth, fifth, sixth and seventh angles are equal.

11. The Internal Reflectance Element of claim 8 wherein said mirrored surfaces are selectively positionable in the x, y and z planes to compensate for the path of said IR beam.

12. The Internal Reflectance Element of claim 8 wherein said transparent optical element and the sample holder are selectively positionable in the x, y and z planes.

13. The Internal Reflectance Element of claim 8 having built in internally reflecting surfaces positioned to internally guide the beam to strike the IRE/sample interface again at said point at said angle and be directed to a detector for analysis.

14. An apparatus for use in Internal Reflectance spectroscopy, comprising:

a transparent sample holder for maintaining a sample in a position for optical and spectroscopic analysis, and movable in the x, y and z planes; whereby an incident light beam from a source can be directed on to said sample, penetrate said sample and said transparent sample holder to be directed to a detector for transmission analysis.

15. An internal reflectance element for use in internal reflectance spectroscopy, comprising:

a transparent element;

a sample holder;

said transparent element having an internal reflectance surface for sample analysis;

said sample holder maintaining a sample in position for optical and spectroscopic analysis at an interface with said transparent element;

said sample holder movable in x, y and z planes relative to said transparent element;

said transparent element, positioned such that an incident light beam entering the transparent element is internally guided to interact with the sample/internal reflectance element interface and is directed to exit said element to a detection system for analysis.

16. A method of spectroscopically analyzing a sample by external reflectance measurements only comprising the steps of directing a light beam for external reflectance only along a light path from a point on a sample support surface to an adjustably positioned mirrored surface external to the support surface, and positioning said adjustable mirrored surface and said support surface relative to each other to guide said reflected light beam to a detection system for analysis.

17. An External Reflectance sample Analysis apparatus for use in external reflectance spectroscopy, comprising:

a reflection-absorption surface;

a sample holder;

said reflection-absorption surface being at a first angle with respect to the x-y plane, said surface being pivotable to change the first angle to a different angle;

said sample holder having a reflection-absorption surface and capable of maintaining a sample in a position for optical and spectroscopic analysis on a surface thereof;

whereby a mirrored surface spaced from said sample surface is positioned to reflect the beam directly or by a second mirrored surface to a condenser assembly on to a detector system for analysis;

said sample holder, reflection-absorption surface and external mirrors being movable in the x, y and z planes.

* * * * *